(12) United States Patent
Delowsky

(10) Patent No.: US 11,944,697 B2
(45) Date of Patent: Apr. 2, 2024

(54) MANUFACTURING PROCESS FOR 2-PHASE SPRAY CONDITIONER

(71) Applicant: Henkel AG & Co. KGaA, Duesseldorf (DE)

(72) Inventor: Jens Delowsky, Norderstedt (DE)

(73) Assignee: HENKEL AG & CO. KGAA, Duesseldorf, NY (US)

( * ) Notice: Subject to any disclaimer, the term of this patent is extended or adjusted under 35 U.S.C. 154(b) by 208 days.

(21) Appl. No.: 17/190,754

(22) Filed: Mar. 3, 2021

(65) Prior Publication Data

US 2021/0290500 A1    Sep. 23, 2021

(51) Int. Cl.
| | | |
|---|---|---|
| *A61K 8/06* | (2006.01) | |
| *A61K 8/89* | (2006.01) | |
| *A61Q 5/12* | (2006.01) | |

(52) U.S. Cl.
CPC ............... *A61K 8/064* (2013.01); *A61K 8/89* (2013.01); *A61Q 5/12* (2013.01); *A61K 2800/5426* (2013.01); *A61K 2800/594* (2013.01); *A61K 2800/596* (2013.01); *A61K 2800/805* (2013.01); *A61K 2800/87* (2013.01)

(58) Field of Classification Search
None
See application file for complete search history.

(56) References Cited

U.S. PATENT DOCUMENTS

| | | | | |
|---|---|---|---|---|
| 6,254,647 | B1 * | 7/2001 | Frohling | A61K 8/06 8/406 |
| 2006/0153790 | A1 * | 7/2006 | Fonolla Moreno | A61K 8/03 424/70.12 |
| 2015/0190317 | A1 * | 7/2015 | Bossant | A61K 8/604 514/25 |

FOREIGN PATENT DOCUMENTS

| | | |
|---|---|---|
| EP | 1267825 A2 | 1/2003 |
| EP | 1676560 A1 | 7/2006 |
| EP | 2168566 A1 | 3/2010 |
| EP | 2444055 A1 | 4/2012 |
| FR | 2880271 A1 | 7/2006 |

* cited by examiner

Primary Examiner — David J Blanchard
Assistant Examiner — Sarah J Chickos
(74) Attorney, Agent, or Firm — Lorenz & Kopf, LLP

(57) ABSTRACT

A process is described for the preparation of a hair treatment composition, which comprises the following process steps:
  a) Providing a water phase (Ia) comprising water and optionally other components and heating the water phase to a temperature of from about 70 to about 95° C.,
  b) Providing an oil phase (Ib) comprising at least one oil and at least one emulsifier, and adding the oil phase to the heated water phase from step a),
  c) Homogenize the mixture from step b),
  d) Cooling the emulsion resulting from step c) to a temperature of from about 35 to about 45° C. and optionally adding further active ingredients,
  e) Filling of the emulsion resulting from step d) into preferably transparent containers, whereby in the resting state after from about 10 to about 90 minutes a separation into a water phase (II) and an emulsion phase (IIb) occurs.

18 Claims, No Drawings

MANUFACTURING PROCESS FOR 2-PHASE SPRAY CONDITIONER

CROSS-REFERENCE TO RELATED APPLICATION

This application claims priority to German Patent Application No. 10 2020 202 673.4, filed Mar. 3, 2020, which is incorporated herein by reference in its entirety.

TECHNICAL FIELD

The present disclosure is in the field of cosmetics and relates to a process for preparing a hair treatment composition having two separate, optically detectable continuous phases with a common horizontal phase boundary.

BACKGROUND

Two-phase hair treatment products have long been known from the state of the art and they are highly appreciated by consumers due to their attractive appearance.

The two phases usually comprise a (transparent) water phase and, as a second layer, either an oil phase or an emulsion phase.

Typically, two-phase hair treatment products are leave-on care products, which are preferably applied to the hair (preferably sprayed) immediately after brief mixing of the two phases.

Mixing of the two phases can be achieved by shaking the agent. This creates an unstable emulsion for a short time, which separates back into the two original phases at rest.

Usually, two-phase hair treatment products are prepared by separately filling a water phase and an oil phase (or an emulsion phase) in the desired weight ratio into suitable containers at room temperature (25° C.).

In EP 2444055, an alternative process is described in which an agent homogeneously mixed at 25° C. is filled into suitable containers and divided into two layers therein.

A problem, especially with two-phase hair treatment agents with an upper emulsion phase and a lower water phase, is that their stability at low temperatures is not always satisfactory. At the phase boundary, for example, undesirable clouding may occur under the influence of cold, or the upper emulsion phase may break and become lumpy.

In the past, special emulsifiers were used to increase the stability of two-phase hair treatment products, but they have not yet eliminated the stability problems mentioned above. In addition, the choice of emulsifiers and/or their amount used and/or their interaction with other ingredients can negatively influence the re-formation of the two phases after the brief mixing. As a result, the sharply separated phases may either take an exceptionally long time to appear or may not appear at all.

BRIEF SUMMARY

Processes for the preparation of a hair treatment composition are provided herein. In accordance with the processes, the compositions are provided in the form of a two-phase system having two separate, optically detectable continuous phases with a common horizontal phase boundary. The processes include the following process steps:
a) Providing a water phase (Ia) comprising water and optionally other components and heating the water phase to a temperature of from about 70 to about 95° C.,
b) Providing an oil phase (Ib) comprising at least one oil and at least one emulsifier, and adding the oil phase to the heated water phase from step a),
c) Homogenizing the mixture from step b),
d) Cooling the emulsion resulting from step c) and optionally adding further active ingredients,
e) Filling the emulsion resulting from step d) into transparent containers, whereby in the resting state after from about 10 to about 90 minutes a separation into a water phase (II) and an emulsion phase (IIb) occurs.

DETAILED DESCRIPTION

The following detailed description is merely exemplary in nature and is not intended to limit the disclosure or the application and uses of the subject matter as described herein. Furthermore, there is no intention to be bound by any theory presented in the preceding background or the following detailed description.

The present application was based on the task of producing a two-phase hair treatment composition comprising an emulsion phase and a water phase, which exhibits excellent stability even under extreme temperature fluctuations without the need for additional emulsifiers to be added to it.

This task was solved by a new production process in which a water phase heated to from about 70 to about 95° C. was first homogenized with an oil phase in a high-shear mixer and, if necessary, further ingredients were added during gradual cooling.

The new manufacturing process has the advantage that the emulsion phase remains stable and unchanged down to −20° C., and that the appearance of the emulsion is significantly improved.

Another advantage of the new manufacturing process is the slowed particle aggregation in the emulsion phase.

A first object of the present disclosure is therefore a process for the preparation of a hair treatment composition in the form of a two-phase system having two separate, optically detectable continuous phases with a common horizontal phase boundary, comprising the following process steps—
a) Providing a water phase (Ia) comprising water and optionally other components and heating the water phase to a temperature of from about 70 to about 95° C., b) Providing an oil phase (Ib) comprising at least one oil and at least one emulsifier, and adding the oil phase to the heated water phase from step a),
c) Homogenize the mixture from step b),
d) Cooling the emulsion resulting from step c) to a temperature of from about 35 to about 45° C. and optionally adding further active ingredients,
e) Filling the emulsion resulting from step d) into preferably transparent containers, whereby in the resting state after from about 10 to about 90 minutes a separation into a water phase (II) and an emulsion phase (IIb) occurs.

Preferably, the water phase (Ia) comprises at least about 90% by weight, preferably about 92.5% by weight, more preferably about 95% by weight and about 97.5% by weight of water, based on the total weight of the water phase (Ia).

The water phase (Ia) may also contain other ingredients such as hair care substances, active ingredients to regulate the pH value and/or preservatives.

In a preferred embodiment, the water phase (Ia) contains at least one hair care substance selected from
cationic polymers and/or
cationic surfactants and/or Protein hydrolysates and/or cationized protein hydrolysates.

In a further preferred embodiment, the water phase (Ia) contains—based on its total weight—from about 0.01 to about 2% by weight, preferably from about 0.05 to about 1.75% by weight, particularly preferably from about 0.1 to about 1.5% by weight and especially preferably from about 0.2 to about 1.25% by weight of at least one cationic polymer.

Suitable cationic polymers are preferably understood to mean cationic polymers known under the INCI designation "polyquaternium".

Particularly suitable cationic polymers are Polyquaternium-6, Polyquaternium-7, Polyquaternium-10, Polyquaternium-11, Polyquaternium-16, Polyquaternium-22, Polyquaternium-24, Polyquaternium-28, Polyquaternium-37, Polyquaternium-67, Polyquaternium-74 and/or Polyquaternium-89.

Cationic polymers derived from polymers of natural origin, such as cellulose, starch or guar polymers, are particularly suitable.

Cationic cellulose derivatives are offered, for example, by the company Amerchol under the name Polymer JR® and cationic guar polymers by the company Rhone-Poulenc or Hercules under the names Jaguar® or N-Hance®.

Other suitable cationic polymers of natural origin are, for example, cationic chitosans, which are commercially available under the names "Kytamer" or "Hydagen", for example.

Also suitable are the cationic polymers known under the INCI designation "quaternium" such as quaternium-8, quaternium-14, quaternium-15, quaternium-18, quaternium-22, quaternium-24, quaternium-26, Quaternium-27, Quaternium-30, Quaternium-33, Quaternium-53, Quaternium-60, Quaternium-61, Quaternium-72, Quaternium-78, Quaternium-80, Quaternium-81, Quaternium-82, Quaternium-83 and/or Quaternium-84.

Other suitable cationic polymers include.
cationic alkyl polyglycosides,
cationized honey, for example the commercial product Honeyquat® 50,
Vinylpyrrolidone-vinylimidazolium methochloride copolymers, as offered under the names Luviquat® FC 370, FC 550, FC 905, and HM 552,
quaternized polyvinyl alcohol
as well as the polymers known under the designations polyquaternium-2, polyquaternium-17, polyquaternium-18, and polyquaternium-27 with quaternary nitrogen atoms in the polymer main chain,
Vinylpyrrolidone-vinylcaprolactam-acrylate terpolymers, as they are commercially available with acrylic acid esters and acrylic acid amides as a third monomer component, for example under the name Aquaflex® SF 40.

Particularly preferably, the water phase (Ia) contains at least one cationic polymer selected from the group of Guar hydroxypropyltrimonium chloride, polyquaternium-10, poly quaternium-11, poly quaternium-16, poly quaternium-37, polyquaternium-67, polyquaternium-74 and/or polyquaternium-89. Polyquaternium-16 is particularly preferred.

In a further preferred embodiment, the water phase (Ia) contains—based on its total weight—from about 0.01 to about 1% by weight of at least one cationic surfactant.

Particularly preferably, the at least one cationic surfactant is used in an amount of from about 0.05 to about 0.8% by weight, very preferably from about 0.075 to about 0.6% by weight and especially from about 0.10 to about 0.5% by weight (based on the total weight of the water phase (Ia)), because it is intended to enhance the hair care effect in the final two-phase hair treatment compositions, but not to prolong the separation into emulsion and water phases.

Suitable cationic surfactants are preferably linear or branched, saturated or unsaturated physiologically compatible $C_1$-$C_{24}$-Alkyltri($C_1$-$C_4$)-alkylammonium salts, Di-$C_1$-$C_{24}$-Alkyldi($C_1$-$C_4$)-alkylammonium salts or Tri-$C_1$-$C_2$-Alkyl($C_1$-$C_4$)-alkylammonium salts and/or primary, secondary, or tertiary amines containing at least one group R—CO(NH)—$(CH_2)_n$—, in which R is a linear or branched, saturated or unsaturated alkyl group containing from about 7 to about 21 carbon atoms and n is an integer of 1 to 4.

Particularly preferred $C_1$-$C_2$-Alkyltri($C_1$-$C_4$)-alkylammonium salts, Di-$C_1$-$C_{24}$-Alkyldi($C_1$-$C_4$)-alkylammonium salts or tri-$C_1$-$C_{24}$-Alkyl($C_1$-$C_4$)-alkylammonium salts are, for example, halide and/or methosulfate salts, in particular chlorides, bromides and/or methosulfates, such as distearyldimethylammonium chloride, lauryltrimethylammonium chloride, lauryltrimethylbenzylammonium chloride, tricetylmethylammonium chloride, cetyltrimethylammonium chloride, cetyltrimethylammonium bromide, cetyltrimethylammonium methosulfate, stearyltrimethylammonium chloride, behenyltrimethylammonium chloride, behenyltrimethylammonium bromide and behenyltrimethylammonium methosulfate.

Cetyltrimethylammonium and behenyltrimethylammonium salts and cetyltrimethylammonium salts containing a methosulfate ion and/or a chloride ion as anion are quite preferred.

Particularly preferred primary, secondary or tertiary amines containing at least one group R—CO(NH)—$(CH_2)_n$—, in which R is a linear or branched, saturated or unsaturated alkyl group containing from about 7 to about 21 carbon atoms, and n is an integer from 1 to 4, are known as "amidoamines".

Suitable amidoamines can be present both as such and (because of protonation in suitably acidic solution) in the form of their corresponding quaternary compound in each case.

Preferred are the non-cationic amidoamines.

Particularly suitable amidoamines, which can be quaternized if necessary, are for example Tego Amid® S18 (Evonik; INCI designation: Stearamidopropyl Dimethylamine), Lexamine® S13 (Inolex; INCI designation: Stearamidopropyl Dimethylamine), Incromine® SB (Croda; INCI designation: Stearamidopropyl Dimethylamine), Witcamine® 100 (Witco, INCI designation: Cocamidopropyl Dimethylamine), Incromine® BB (Croda, INCI designation: Behenamidopropyl Dimethylamine), ProCondition® 22 (Inolex, INCI designation: Brassicamidopropyl Dimethylamine), Mackine® 401 (McIntyre, INCI designation: Isostearylamidopropyl Dimethylamine) and other Mackine grades as well as Adogen® S18V (Witco, INCI designation: Stearylamidopropyl Dimethylamine).

Examples of permanent cationic amidoamines that can be used are: Rewoquat® RTM 50 (Witco Surfactants GmbH, INCI designation: Ricinoleamidopropyltrimonium Methosulfate), Empigen® CSC (Albright & Wilson, INCI designation: Cocamidopropyltrimonium Chloride), Swanol Lanoquat® DES-50 (Nikko, INCI designation: Quatemium-33), Rewoquat® UTM 50 (Witco Surfactants GmbH, Undecyleneamidopropyltrimonium Methosulfate).

Stearamidopropyl dimethylamines and/or brassicamidopropyl dimethylamines are particularly preferred.

In a first particularly preferred embodiment, the water phase (Ia) contains, based on its total weight—
- from about 0.01 to about 2% by weight of at least one cationic polymer and/or
- from about 0.01 to about 1% by weight of at least one cationic surfactant.

Within this embodiment, it is particularly preferred when the water phase (Ia)—based on its total weight is—
- from about 0.01 to about 2% by weight of at least one cationic polymer and
- from about 0.01 to about 1% by weight of at least one cationic surfactant.

Within this embodiment, it is particularly preferred if the water phase (Ia)—based on its total weight contains—
- from about 0.01 to about 2% by weight of at least one cationic polymer known under the INCI name polyquaternium-16 and
- from about 0.01 to about 1% by weight of at least one cationic surfactant known by the INCI designation cetrimonium chloride.

In a further preferred embodiment, the water phase (Ia) contains—based on its total weight—from about 0.001 to about 1% by weight, preferably from about 0.005 to about 0.75% by weight, particularly preferably from about 0.01 to about 0.5% by weight and especially preferably from about 0.02 to about 0.25% by weight of at least one protein hydrolysate.

Suitable protein hydrolysates (PH) include PH of plant as well as animal, marine or synthetic origin.

Preferred animal protein hydrolysates include elastin, collagen, keratin, silk, and milk protein hydrolysates, which may also be in the form of salts. Such products are marketed, for example, under the trademarks Dehylan® (Cognis), Promois® (Interorgana), Collapuron® (Cognis), Nutrilan® (Cognis), Gelita-Sol® (Deutsche Gelatine Fabriken Stoess & Co), Lexein® (Inolex), ProSina® and Kerasol® (Croda).

Preferred vegetable protein hydrolysates include soy, almond, pea, potato, and wheat protein hydrolysates. Such products are available, for example, under the trademarks Gluadin® (Cognis), DiaMin® (Diamalt), Lexein® (Inolex), Hydrosoy® (Croda), Hydrolupin® (Croda), Hydrosesame® (Croda), Hydrotritium® (Croda) and Crotein® (Croda).

Suitable protein hydrolysates of marine origin include, for example, collagen hydrolysates from fish or algae as well as protein hydrolysates from mussels or pearl hydrolysates. Examples of pearl hydrolysates suitable as contemplated herein are the commercial products Pearl Protein Extract BG® or Crodarom® Pearl.

Suitable cationized protein hydrolysates can also be of animal, plant, or marine origin.

Quaternization of protein hydrolysates or amino acids can be carried out with quaternary ammonium salts such as N,N-Dimethyl-N-(n-Alkyl)-N-(2-hydroxy-3-chloro-n-propyl)-ammonium halides. In addition, the cationic protein hydrolysates may also be further derivatized.

Typical examples of particularly suitable cationic protein hydrolysates and/or their derivatives are the products known under the INCI designations and commercially available: Cocodimonium Hydroxypropyl Hydrolyzed Collagen, Cocodimonium Hydroxypropyl Hydrolyzed Casein, Cocodimonium Hydroxypropyl Hydrolyzed Collagen, Cocodimonium Hydroxypropyl Hydrolyzed Hair Keratin, Cocodimonium Hydroxypropyl Hydrolyzed Keratin, Cocodimonium Hydroxypropyl Hydrolyzed Rice Protein, Cocodimonium Hydroxypropyl Hydrolyzed Silk, Cocodimonium Hydroxypropyl Hydrolyzed Soy Protein, Cocodimonium Hydroxypropyl Hydrolyzed Wheat Protein, Cocodimonium Hydroxypropyl Silk Amino Acids, Hydroxypropyl Arginine Lauryl/Myristyl Ether HCl, Hydroxypropyltrimonium Gelatin, Hydroxypropyltrimonium Hydrolyzed Casein, Hydroxypropyltrimonium Hydrolyzed Collagen, Hydroxypropyltrimonium Hydrolyzed Conchiolin Protein, Hydroxypropyltrimonium Hydrolyzed keratin, Hydroxypropyltrimonium Hydrolyzed Rice Bran Protein, Hydroxyproypltrimonium Hydrolyzed Silk, Hydroxypropyltrimonium Hydrolyzed Soy Protein, Hydroxypropyl Hydrolyzed Vegetable Protein, Hydroxypropyltrimonium Hydrolyzed Wheat Protein, Hydroxypropyltrimonium Hydrolyzed Wheat Protein/Siloxysilicate, Laurdimonium Hydroxypropyl Hydrolyzed Soy Protein, Laurdimonium Hydroxypropyl Hydrolyzed Wheat Protein, Laurdimonium Hydroxypropyl Hydrolyzed Wheat Protein/Siloxysilicate, Lauryldimonium Hydroxypropyl Hydrolyzed Casein, Lauryldimonium Hydroxypropyl Hydrolyzed Collagen, Lauryldimonium Hydroxypropyl Hydrolyzed Keratin, Lauryldimonium Hydroxypropyl Hydrolyzed Silk, Lauryldimonium Hydroxypropyl Hydrolyzed Soy Protein, Steardimonium Hydroxypropyl Hydrolyzed Casein, Steardimonium Hydroxypropyl Hydrolyzed Collagen, Steardimonium Hydroxypropyl Hydrolyzed Keratin, Steardimonium Hydroxypropyl Hydrolyzed Rice Protein, Steardimonium Hydroxypropyl Hydrolyzed Silk, Steardimonium Hydroxypropyl Hydrolyzed Soy Protein, Steardimonium Hydroxypropyl Hydrolyzed Vegetable Protein, Steardimonium Hydroxypropyl Hydrolyzed Wheat Protein, Steartrimonium Hydroxyethyl Hydrolyzed Collagen, Quaternium-76 Hydrolyzed Collagen, Quaternium-79 Hydrolyzed Collagen, Quaternium-79 Hydrolyzed Keratin, Quaternium-79 Hydrolyzed Milk Protein, Quatemium-79 Hydrolyzed Silk, Quaternium-79 Hydrolyzed Soy Protein, Quaternium-79 Hydrolyzed Wheat Protein.

Keratin, silk, milk protein, wheat and/or soy protein hydrolysates, which may be quaternized, are particularly preferred. Keratin and/or wheat and/or silk protein hydrolysates, which may be quaternized, are particularly preferred.

The—optionally quaternized—protein hydrolysates can be used in the hair treatment compositions of the present disclosure both individually and as a mixture.

It may be advantageous for some embodiments of the present disclosure if the water phase (Ia) comprises at least one protein hydrolysate of animal or plant origin and at least one quaternized protein hydrolysate of animal or plant origin.

For the purposes of the present disclosure, suitable active ingredients for regulating the pH are preferably understood to mean carboxylic acids such as, for example, acetic acid, citric acid, malic acid, maleic acid, formic acid, amidosulfonic acid, phosphoric acid, phosphonic acids, D-lactic acid, L-lactic acid, D/L-lactic acid and/or oxalic acid, or alkalis such as sodium hydroxide solution. Advantageously, they are used in amounts of from about 0.01-2 wt. %, preferably from about 0.01-1.5 wt. % and from about 0.01 to about 1 wt. % (based on the total weight of the water phase (Ia)).

Suitable preservatives in the sense of the present disclosure are preferably aromatic alcohols and/or aromatic carboxylic acids or salts thereof, such as phenoxyethanol and/or sodium benzoate. They can be used in a proportion by weight of up to about 1% (based on the total weight of the water phase (Ia).

It is advantageous if water is mixed with all other optional ingredients and the resulting water phase (Ia) is subsequently heated to a temperature of from about 70 to about (step a) of the process as contemplated herein).

In a particularly preferred embodiment, the water phase (Ia) is heated to a temperature in the range of from about 75 to about 90° C., preferably from about 80 to about 90° C., in step a) of the process as contemplated herein.

The oil phase (Ib) comprises at least one oil and at least one emulsifier.

Suitable oils within the meaning of the present disclosure are preferably understood to be oils which have a melting point of less than about 45° C., preferably less than about 40° C., more preferably less than about 35° C. and less than about 30° C., and which are free flowing.

Examples of particularly suitable oils in the sense of the present disclosure are:

i. Silicones such as polyalkylsiloxanes, polyarylsiloxanes and/or polyalkylarylsiloxanes, which may be volatile or non-volatile, straight-chain, branched or cyclic; particularly preferred in the sense of the present disclosure are volatile, cyclic siloxanes, siloxanes known under the INCI designation cyclomethicone, and polyarylsiloxanes, siloxanes known under the INCI designation phenyl trimethicone.

ii. polysiloxanes substituted with amino groups and/or with hydroxyl groups; particularly preferred in the sense of the present disclosure are polysiloxanes substituted with hydroxyl groups and compounds known under the INCI designation dimethiconol.

iii. Esters of linear or branched, saturated or unsaturated fatty alcohols containing from about 2 to about 30 carbon atoms with linear or branched, saturated or unsaturated fatty acids which may be hydroxylated and contain from about 2 to about 30 carbon atoms, for example 2-ethylhexyl palmitate (e.g. Cegesoft® C 24), hexyldecyl stearate (Eutanol® G 16), hexyldecyl laurate, isodecyl neopentanoate, isononyl isononanoate, 2-ethylhexyl stearate, isopropyl myristate, Isopropyl palmitate, isopropyl stearate, isopropyl isostearate, isopropyl oleate, isooctyl stearate, isononyl stearate, isocetyl stearate, isononyl isononanoate, isotridecyl isononanoate, Cetearyl isononanoate, 2-ethylhexyl laurate, 2-ethylhexyl isostearate, 2-ethylhexyl cocoate, 2-octyl dodecyl palmitate, butyloctanoic acid 2-butyloctanoate, diisotridecyl acetate, n-butyl stearate, n-hexyl laurate, n-decyl oleate, oleyl oleate, oleyl glucate, erucyl oleate, erucyl glucate, ethylene glycol dioleate and dipalmitate, and mixtures thereof;

iv. Benzoic acid esters of linear or branched $C_8$-$C_{22}$-alkanols, preferably $C_{12}$-$C_{15}$ alkyl benzoates, for example the commercial products Finsolv® TN, Finsolv® SB, ethylhexyl benzoate and/or isostearyl benzoate.

v. $C_8$-$C_{22}$-fatty alcohol esters of monohydric or polyhydric $C_2$-$C_7$ hydroxycarboxylic acids, for example esters of glycolic acid, lactic acid, malic acid, tartaric acid, citric acid and salicylic acid, and mixtures thereof, such as the commercial products Cosmacol® EMI, Cosmacol® ESI and Cosmacol® ETI.

vi. branched, saturated or unsaturated fatty alcohols containing from about 6 to about 30 carbon atoms, for example hexyldecanol (e.g., Eutanol® G), octyldodecanol and 2-ethylhexyl alcohol, and mixtures thereof vii. Dicarboxylic acid esters of linear or branched $C_2$-$C_{10}$ alkanols, for example Diisopropyl adipate, di-n-butyl adipate, di-(2-ethylhexyl) adipate, dioctyl adipate, diethyl/di-n-butyl/dioctyl sebacate, diisopropyl sebacate, dioctyl malate, dioctyl maleate, dicaprylyl maleate, diisooctyl succinate, di-2-ethylhexyl succinate and di-(2-hexyldecyl) succinate, and mixtures thereof viii. Di-n-alkyl ethers having a total of from about 12 to about 36, preferably from about 12 to about 24, carbon atoms, for example Di-n-octyl ether (e.g., Cetiol® OE), di-n-decyl ether, n-hexyl-n-octyl ether and n-octyl-n-decyl ether, and mixtures thereof ix. Kerosene and/or isoparaffins; for example, isoparaffins with from about 9 to about 17 carbon atoms such as isodecane, isoundecane, isododecane, isotridecane, isotetradecane and mixtures of these isoparaffins and/or kerosene's with from about 9 to about 23 carbon atoms.

x. vegetable oils, for example, amaranth seed oil, apricot kernel oil, argan oil, avocado oil, babassu oil, cottonseed oil, borage seed oil, camelina oil, safflower oil, peanut oil, pomegranate seed oil, grapefruit seed oil, hemp oil, rosehip seed oil, hazelnut oil, elderberry seed oil, currant seed oil, jojoba oil, cocoa butter, linseed oil, macadamia nut oil, corn oil, almond oil, manila oil, evening primrose oil, olive oil, palm oil, peach kernel oil, rapeseed oil, rice oil, sea buckthorn fruit oil, sea buckthorn kernel oil, sesame oil, shea butter, soybean oil, sunflower oil, grape seed oil, walnut oil or wild rose oil.

The proportion by weight of the at least one oil in the total weight of the oil phase (Ib) is preferably at least about 85% by weight, more preferably about 87.5% by weight, particularly preferably about 90% by weight and especially about 92.5% by weight.

In a particularly preferred embodiment, the oil phase (Ib) comprises at least one silicone in a proportion by weight of at least about 50% of the total weight of the oil phase (Ib), preferably selected from cyclic siloxanes, polyarylsiloxanes and/or hydroxyl-substituted polysiloxanes.

Within this embodiment, it is particularly preferred if the oil phase (Ib) comprises at least one silicone in a proportion by weight of at least about 60% of the total weight of the oil phase (Ib), preferably selected from cyclic siloxanes, polyarylsiloxanes and hydroxyl-substituted polysiloxanes.

Within this embodiment, it is particularly preferred if the oil phase (Ib) comprises at least one silicone in a proportion by weight of at least about 70% of the total weight of the oil phase (Ib), preferably selected from compounds known under the INCI designation cyclomethicone, phenyl trimethicone and dimethiconol.

Suitable emulsifiers for the oil phase (Ib) are preferably W/O emulsifiers, particularly preferably silicone-based W/O emulsifiers and especially preferably $C_8$-$C_{30}$ alkyl PEG-x/PPG-y dimethicones.

The degree of ethoxylation is preferably from about 2 to about 20, more preferably from about 3 to about 17, and especially preferably from about 7 to about 12.

The degree of propoxylation is preferably from 0 to about 15, more preferably from 0 to about 10 and especially preferably from 0 to about 5.

The alkyl group preferably has from about 8 to about 30, more preferably from about 8 to about 24, and especially preferably from about 10 to about 20 carbon atoms.

Examples of particularly suitable emulsifiers are the products known under the INCI designation Cetyl PEG/PPG-10/1 dimethicone and commercially available, for example, under the designations Abil® EM 90 or Microcare® Silicone E 1016.

The proportion by weight of the at least one emulsifier in the total weight of the oil phase (Ib) is preferably from about 1-15% by weight, more preferably from about 1.5-12.5% by weight, particularly preferably from about 2-10% by weight and especially from about 2.5-7.5% by weight.

In another particularly preferred embodiment, the oil phase (Ib) comprises at least one W/O emulsifier in a proportion by weight of from about 1 to about 15% by weight of the total weight of the oil phase (Ib), preferably a silicone-based W/O emulsifier.

It was found that homogenization step c) is necessary to achieve the best possible stability of the two-phase hair treatment agent.

Preferably, homogenization in step c) is carried out at elevated temperatures in the range of from about 70 to about 80° C. and in a high shear rate mixer.

As contemplated herein, high shear rate is preferably understood to mean from about 2000 to about 10000 rpm, more preferably from about 2500 to about 8000 rpm, particularly preferably from about 3000 to about 6000 rpm and especially from about 3500 to about 5000 rpm, the homogenization time per kg of product being preferably from about 1-4 minutes, particularly preferably from about 2-3 minutes.

Suitable for use in the processes as contemplated herein are, for example, high shear mixers known under the trade name Polytron® (such as Polytron® 6100).

In another preferred embodiment, the homogenization of the water phase (Ia) and the oil phase (Ib) in step c) is carried out with a high shear mixer at a temperature in the range of from about 70 to about 80° C.

As contemplated herein, it is advantageous if the homogenized mixture from process step c) is first cooled before further ingredients are added.

Preferably, the emulsion resulting from step c) is cooled to a temperature of from about 35 to about 45° C., more preferably from about 37 to about 43° C., before further active ingredients are added.

The active ingredients that can be added in step d) are preferably perfume oils and/or vitamins, vitamin precursors and/or vitamin derivatives and/or protein hydrolysates and/or cold-pressed oils.

Suitable protein hydrolysates and/or cold-pressed oils (vegetable oils) have already been described earlier.

In another preferred embodiment, the emulsion is cooled in step d) to a temperature in the range of from about 35 to about 45° C., preferably from about 37 to about 43° C.

In another preferred embodiment, perfume oils and/or vitamins, vitamin precursors and/or vitamin derivatives are added to the emulsion in step d) after cooling.

The percentage by weight of perfume oils in the total weight of the two-phase hair treatment composition is preferably from about 0.01 to about 5% by weight, more preferably from about 0.05 to about 3% by weight, and most preferably from about 0.1 to about 1% by weight.

Suitable vitamins are vitamins, provitamins and vitamin precursors as well as their derivatives from the groups A, B, C, E, F and H.

The group of substances known as vitamin A includes retinol (vitamin $A_1$) and 3,4-didehydroretinol (vitamin $A_2$). The β-carotene is the provitamin of retinol. Examples of vitamin A components include vitamin A acid and its esters, vitamin A aldehyde and vitamin A alcohol, and its esters such as palmitate and acetate. The two-phase hair treatment compositions may preferably contain the vitamin A component in amounts of from about 0.005-1% by weight, based on the total composition.

The vitamin B group or complex includes, among others.
Vitamin $B_1$ (Thiamine)—
Vitamin $B_2$ (Riboflavin)
Vitamin $B_3$. The compounds nicotinic acid and nicotinamide (niacinamide) are frequently listed under this designation. Preferably, nicotinic acid amide, which may be present in the two-phase hair treatment composition preferably in amounts of from about 0.005 to about 1% by weight, based on the total composition.
Vitamin B5 (pantothenic acid, panthenol and pantolactone).
Within this group, the panthenol and/or pantolactone is preferred. Usable derivatives of panthenol are the esters and ethers of panthenol as well as cationically derivatized panthenols. Individual representatives include panthenol triacetate, panthenol monoethyl ether and its monoacetate as well as cationic panthenol derivatives. The above-mentioned compounds of the vitamin B5 type may preferably be present in the two-phase hair treatment compositions in amounts of from about 0.05-5% by weight, based on the total composition. Amounts of from about 0.1-2% by weight are particularly preferred.
Vitamin $B_6$ (pyridoxine as well as pyridoxamine and pyridoxal)
Vitamin $B_7$-cf. vitamin H.
Vitamin C (Ascorbic acid). Vitamin C can preferably be used in the two-phase hair treatment compositions in amounts of from about 0.01 to about 3% by weight, based on the total composition. Use in the form of the palmitic acid ester, glucosides or phosphates may be preferred. Use in combination with tocopherols may also be preferred.
Vitamin E (tocopherols, especially α-tocopherol). Tocopherol and its derivatives, which include the esters such as the acetate, the nicotinate, the phosphate, and the succinate, may preferably be present in the two-phase hair treatment compositions in amounts of from about 0.005-1% by weight, based on the total composition.
Vitamin F. The term "vitamin F" usually refers to essential fatty acids, especially linoleic acid, linolenic acid, and arachidonic acid.
Vitamin H. The compound (3 aS,4S,6aR)-2-oxohexahydrothienol[3,4-d]imidazole-4-valeric acid is known as vitamin H, but the trivial name biotin has since become established. Biotin may preferably be present in the two-phase hair treatment compositions in amounts of from about 0.0001 to about 1.0% by weight, in amounts of from about 0.001 to about 0.01% by weight.

Particularly preferably, the two-phase hair treatment compositions as contemplated herein may contain vitamins, provitamins and vitamin precursors from the groups A, B, E and H. Panthenol, pantolactone, nicotinic acid amide and vitamin E acetate are particularly preferred and can be added to the two-phase hair treatment compositions as contemplated herein both individually and in their combination in the previously mentioned amounts.

The emulsion resulting from step d) is filled into preferably transparent containers and allowed to further cool. At rest, a separation into a water phase (II) and an emulsion phase (IIb) can be seen after from about 10 to about 90 minutes.

In a preferred embodiment, the separation into an emulsion phase (IIa) and a water phase (IIb) takes place after from about 10 to about 60 minutes, preferably after from about 15 to about 45 minutes and after from about 20 to about 40 minutes.

By the process as contemplated herein, visually appealing two-phase products are obtainable, which can be—
mixed quickly and easily by shaking,
simply spray onto the hair (in case the two-phase hair treatment products are filled into a pump dispenser), and at rest within a short time into an attractive two-phase product with a sharp horizontal phase boundary with stable emulsion phase (IIb) and water phase (II).

In a further preferred embodiment, a two-phase hair treatment composition obtainable by the process as contemplated herein comprises, in the resting state.
- i. a water phase (II) in a proportion by weight of at least about 75%, preferably at least about 80% and in particular at least about 85% by weight of the total weight of the two-phase hair treatment composition, and
- ii. an emulsion phase (IIb) in a proportion by weight of at most about 25%, preferably at most about 20% and at most about 15% by weight of the total weight of the two-phase hair treatment composition.

For better recognition of the mixing and demixing of the emulsion phase (IIb) and the water phase (II), it can be advantageous if the water phase (II) is transparent and the emulsion phase (IIb) is opaque to milky cloudy.

In the context of the present disclosure, "transparency" is understood to mean that the water phase (IIa) in the quiescent state preferably has an NTU (Nephelometric Turbidity Unit) value of no more than about 100, preferably no more than about 75, more preferably no more than about 50, and no more than about 25 (measured, for example, with a Turbiquant® type turbidimeter from Merck).

Also, for better visualization, the water phase (II) may be dyed with a cosmetically acceptable dye.

It is further desirable and preferred that the two-phase hair treatment compositions of the present disclosure are sprayable.

In sprayable form, the two-phase hair treatment compositions of the present disclosure are suitable for application from a pump dispenser. The advantage of such a form of application is that it is simple, clean, and timesaving to use, because the two-phase hair treatment agents can be distributed as a fine spray from a suitable pump dispenser by simply operating a pump valve and reach all areas of the hair.

In this way, the hands do not meet the agent and do not need to be cleaned after applying the agent.

For such a form of application, the two-phase hair treatment compositions as contemplated herein which are ready for use (i.e., homogenized by shaking) preferably have a viscosity of not more than about 1000 mPas, preferably of not more than about 800 mPas, more preferably of not more than about 600 mPas and of not more than about 500 mPas (in each case measured at about 20° C. with a Brookfield viscometer Dy-II, spindle from about 2 at about 20 rpm).

Also preferred for such a form of application is that the two-phase hair treatment agents are free of propellants.

Examples

The following two-phase hair treatment compositions were prepared by the method as contemplated herein (the amounts refer to wt %):

|  | 1 | 2 | 3 |
|---|---|---|---|
| Water phase (Ia) | | | |
| Cetrimonium Chloride | 0.05-0.5 | 0.05-0.5 | 0.05-0.5 |
| Polyquaternium-16 | 0.1-1 | 0.1-1 | 0.1-1 |
| Hydrolyzed Keratin | 0.001-0.05 | | 0.001-0.05 |

-continued

|  | 1 | 2 | 3 |
|---|---|---|---|
| Steardimonium Hydroxypropyl Hydrolyzed Keratin | 0.01-0.5 | 0.01-0.5 | 0.01-0.5 |
| Citric Acid | 0.1-1 | | 0.1-1 |
| Lactic acid | | 0.1-1 | |
| PEG-7 Glyceryl cocoate | | | 0.05-1 |
| Water | ad 100 | ad 100 | ad 100 |
| Oil phase (Ib) | | | |
| Cyclomethicone | 3-7 | 3-7 | 3-7 |
| Phenyl Trimethicone | 0.1-2 | 0.1-2 | 0.1-2 |
| Dimethiconol | 0.05-1 | 0.05-1 | 0.05-1 |
| Cetyl PEG/PPG-10/1 dimethicone | 0.05-1 | 0.05-1 | 0.05-1 |
| Apricot kernel oil | | | 0.01-1 |
| Argan oil | | 0.01-1 | |
| Shea butter | | | 0.01-1 |
| Perfume | 0.1-1 | 0.1-1 | 0.1-1 |
| pH value | 3.0-4.5 | 3.0-4.5 | 3.0-4.5 |

The components of the water phase (Ia) were mixed and heated to 80 to 90° C.

The components of the oil phase (Ib)—except for the vegetable (preferably cold-pressed) oil(s) and the perfume oil—were mixed with the water phase (Ia). Oil(s) and the perfume oil—were mixed, added to the water phase (Ia) and the resulting mixture was homogenized at a temperature of 70 to 80° C. in a high shear mixer (Polytron® 6100).

The homogenized mixture was cooled to a temperature of 37 to 43° C., then the vegetable oil(s) (preferably cold-pressed) and/or perfume oil(s) were added to the homogenized mixture with stirring, and the emulsions were filled into suitable (preferably transparent) containers. At rest, the emulsions separated into a water phase (II) and an emulsion phase (IIb) after a maximum of 45 minutes.

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the various embodiments in any way. Rather, the foregoing detailed description will provide those skilled in the art with a convenient road map for implementing an exemplary embodiment as contemplated herein. It being understood that various changes may be made in the function and arrangement of elements described in an exemplary embodiment without departing from the scope of the various embodiments as set forth in the appended claims.

The invention claimed is:

1. A process for the preparation of a hair treatment composition in the form of a two-phase system having two separate, optically detectable continuous phases with a common horizontal phase boundary, comprising the following process steps:
   a) Providing a water phase (Ia) comprising water and optionally other components and heating the water phase to a temperature of from about 70 to about 95° C., wherein the water phase (Ia)—based on its total weight—comprises:
      from about 0.01 to about 2% by weight of at least one cationic polymer and/or
      from about 0.01 to about 1% by weight of at least one cationic surfactant,
   b) Providing an oil phase (Ib) comprising at least one oil and at least one emulsifier, and adding the oil phase to the heated water phase from step a), c) Homogenizing the mixture from step b),
d) Cooling the emulsion resulting from step c) and optionally adding further active ingredients,
e) Filling the emulsion resulting from step d) into transparent containers, whereby in the resting state after from about 10 to about 90 minutes a separation into a water phase (IIa) and an emulsion phase (IIb) occurs.

2. A process according to claim 1, wherein the water phase (Ia) in step a) is heated to a temperature in the range of from about 75 to about 90° C.

3. A process according to claim 1, in which the oil phase (Ib) comprises a silicone in a proportion by weight of at least about 50% of the total weight of the oil phase (Ib).

4. A process according to claim 1, in which the oil phase (Ib) comprises at least one W/O emulsifier in a proportion by weight of from about 1 to about 15% by weight of the total weight of the oil phase (Ib).

5. A process according to claim 1, wherein the homogenization of the water phase (Ia) and the oil phase (Ib) in step c) is carried out with a high shear mixer at a temperature in the range of from about 70 to about 80° C.

6. A process according to claim 1, wherein the emulsion in step d) is cooled to a temperature in the range of from about 35 to about 45° C.

7. A process according to claim 6, wherein perfume oils and/or vitamins, vitamin precursors and/or vitamin derivatives are added to the emulsion in step d) after cooling.

8. A process according to claim 1, in which the separation into an emulsion phase and a water phase in step e) occurs after from about 10 to about 60 minutes.

9. A process according to claim 1, in which the hair treatment composition in the resting state is—
a water phase in a proportion by weight of at least about 75%, and
an emulsion phase in a proportion by weight of at most 25%.

10. A process according to claim 1, wherein the water phase (Ia) in step a) is heated to a temperature in the range of from about 80 to about 90° C.

11. A process according to claim 1, in which the oil phase (Ib) comprises a silicone in a proportion by weight of at least 50% of the total weight of the oil phase (Ib), wherein the silicone is selected from cyclic siloxanes, polyarylsiloxanes, hydroxyl-substituted polysiloxanes, or combinations thereof.

12. A process according to claim 1, in which the oil phase (Ib) comprises at least one silicone-based W/O emulsifier in a proportion by weight of from about 1 to about 15% by weight of the total weight of the oil phase (Ib).

13. A process according to claim 1, wherein the emulsion in step d) is cooled to a temperature in the range of from about 37 to about 43° C.

14. A process according to claim 1, in which the separation into an emulsion phase and a water phase in step e) occurs after a maximum of 45 minutes.

15. A process according to claim 1, in which the hair treatment composition in the resting state is—
a water phase in a proportion by weight of at least 80% by weight of the total weight of the hair treatment composition, and
an emulsion phase in a proportion by weight of at most 20% by weight of the total weight of the hair treatment composition.

16. A process according to claim 1, in which the hair treatment composition in the resting state is—
a water phase in a proportion by weight of at least 85% by weight of the total weight of the hair treatment composition, and
an emulsion phase in a proportion by weight of at most 15% by weight of the total weight of the hair treatment composition.

17. A process for the preparation of a hair treatment composition in the form of a two-phase system having two separate, optically detectable continuous phases with a common horizontal phase boundary, comprising the following process steps:
a) Providing a water phase (Ia) comprising water and optionally other components and heating the water phase to a temperature of from about 80 to about 90° C.,
b) Providing an oil phase (Ib) comprising a silicone in a proportion by weight of at least 50% of the total weight of the oil phase (Ib), wherein the silicone is selected from cyclic siloxanes, polyarylsiloxanes, hydroxyl-substituted polysiloxanes, or combinations thereof, and adding the oil phase to the heated water phase from step a),
c) Homogenizing the mixture from step b) with a high shear mixer at a temperature in the range of from about 70 to about 80° C.,
d) Cooling the emulsion resulting from step c) to a temperature of from about 37 to about 43° C. and optionally adding further active ingredients,
e) Cooling the emulsion resulting from step d) and filling into transparent containers, whereby in the resting state after a maximum of 45 minutes a separation into a water phase (II) and an emulsion phase (IIb) occurs.

18. A process for the preparation of a hair treatment composition in the form of a two-phase system having two separate, optically detectable continuous phases with a common horizontal phase boundary, comprising the following process steps:
a) Providing a water phase (Ia) comprising water and optionally other components and heating the water phase to a temperature of from about 70 to about 95° C.,
b) Providing an oil phase (Ib) comprising at least one oil and at least one emulsifier, wherein the oil phase (Ib) comprises a silicone in a proportion by weight of at least about 50% of the total weight of the oil phase (Ib), and adding the oil phase to the heated water phase from step a),
c) Homogenizing the mixture from step b),
d) Cooling the emulsion resulting from step c) and optionally adding further active ingredients,
e) Filling the emulsion resulting from step d) into transparent containers, whereby in the resting state after from about 10 to about 90 minutes a separation into a water phase (IIa) and an emulsion phase (IIb) occurs.

* * * * *